United States Patent [19]

Boesten

[11] 4,172,846

[45] Oct. 30, 1979

[54] PROCESS FOR SEPARATING A MIXTURE OF AN OPTICALLY ACTIVE PHENYLGLYCINE AMIDE AND AN OPTICALLY ACTIVE PHENYLGLYCINE

[75] Inventor: Wilhelmus H. J. Boesten, Sittard, Netherlands

[73] Assignee: Stamicarbon, B.V., Geleen, Netherlands

[21] Appl. No.: 843,492

[22] Filed: Oct. 19, 1977

[30] Foreign Application Priority Data

Nov. 10, 1976 [NL] Netherlands ................... 7612456

[51] Int. Cl.² ............................................. C07C 103/28
[52] U.S. Cl. ......................... 260/558 A; 260/559 A; 562/437; 562/444; 562/449; 562/443
[58] Field of Search .......... 260/558 A, 559 A, 562 N, 260/561 A, 518 R, 518 A

[56] References Cited

U.S. PATENT DOCUMENTS

| | | | |
|---|---|---|---|
| 3,971,700 | 7/1976 | Boesten | 195/2 |
| 3,976,680 | 8/1976 | Clark et al. | 560/38 |
| 4,036,852 | 7/1977 | Boesten | 260/558 A X |
| 4,072,698 | 2/1978 | Hylton et al. | |
| 4,093,653 | 6/1978 | Boesten | 260/558 A |
| 4,094,904 | 6/1978 | Boesten | 260/558 A |

*Primary Examiner*—Thomas Waltz
*Attorney, Agent, or Firm*—Cushman, Darby & Cushman

[57] ABSTRACT

A process is disclosed for the separation of a mixture of an optically active α-phenylglycine amide and the corresponding optically active α-phenylglycine acid, through the formation of a novel Schiff base of at least the amide, and achieving the separation with the resulting solubility differences while substantially completely avoiding racemization.

11 Claims, No Drawings

PROCESS FOR SEPARATING A MIXTURE OF AN OPTICALLY ACTIVE PHENYLGLYCINE AMIDE AND AN OPTICALLY ACTIVE PHENYLGLYCINE

The invention relates to processes for the preparation of optically active α-phenylglycine compounds (e.g., α-amino phenyl acetic acids) and, in particular, to a process for separating a mixture of an optically active α-phenylglycine amide and an optically active α-phenylglycine. In this process no noticeable racemization takes place and separation of the optically active components of said mixture is easily achieved.

This invention further provides novel compounds constituting Schiff base derivatives of α-phenylglycine amide, which are useful in said process.

BACKGROUND OF THE INVENTION

Useful and desirable chemical products are the optically active α-phenylglycine compounds. For instance, D-α-phenylglycine is useful for the preparation of α-aminobenzyl penicillin, and L-α-phenylglycine is useful for the preparation of asparagine-L-α-phenylglycine methyl ester (a sweetening agent).

It is already known that mixtures of these optically active phenylglycine amides and optically active phenylglycines can be obtained by the selective enzymatic hydrolytic conversion of DL phenylglycine amides, as applicant has previously disclosed in his U.S. Pat. No. 3,971,700 (the disclosure of which is incorporated herein by reference). It has also been shown that such a mixture can be separated into its respective optically active components by means of ion-exchange column techniques. However, for industrial practice, where long residence times are involved in the use of ion-exchanger columns, this method is difficult to apply without racemization of the product taking place.

OBJECTS OF THE INVENTION

It is principally an object of this invention to provide an improved process for the separation of a mixture of optically active phenylglycines and phenylglycine amides, which, in particular, minimizes racemization of said mixture.

A further objection of the invention is to provide, as novel compounds, the benzaldehyde Schiff base derivatives of phenylglycine amides for use in said process.

Still a further object of the invention is to provide a process for the separation of a mixture optically active phenylglycine amides and optically active phenylglycines, which can be carried out without noticeable racemization, by first converting the compounds to be separated into a Schiff base, and then separating, by solubility, said Schiff bases.

DESCRIPTION OF THE INVENTION

According to the present invention, the separation of optically active phenylglycine amides and optically active phenylglycines (which may carry a substituent on the benzene nucleus) is characterized in that the Schiff base of at least the optically active phenylglycine amides and optionally also of the optically active phenylglycines is (are) formed with a benzaldehyde compound, (which may be a benzaldehyde carrying a substituent on the benzene ring), and after separating at least the Schiff base of the phenylglycine amide, recovering the optically active phenylglycine compounds from the Schiff base or bases.

A principal advantage of this process is that the optically active phenylglycine compounds are not racemized during this procedure. They can thus be easily isolated in high state of optical purity. The use of benzaldehyde has the added advantage that the benzaldehyde is itself a starting compound for the preparation of phenylglycine amides via the acid hydrolysis of the corresponding α-phenylglycine nitrile (see, e.g., U.S. Pat. No. 3,971,700). Further, the separation of the Schiff base derivatives and the later recovery of benzaldehyde therefrom are easy to perform. Still another advantage in the use of benzaldehyde derives from its substantial immiscibility with water, and the very favorable partition coefficients resulting from the solubility of the phenylglycine amide Schiff base in benzaldehyde and of the phenylglycine or its Schiff base in an aqueous system. Thus, the benzaldehyde Schiff base of the optically active phenylglycine amides substantially completely dissolves in the benzaldehyde layer, while the optically active phenylglycine component, either as the free amino acid or as the Schiff base derivative thereof, remains substantially completely in solution in the aqueous layer phase. For these reasons, such benzaldehyde is a preferred extracting agent.

The glycine derivatives which may be used in the practice of this invention include those of the general formula

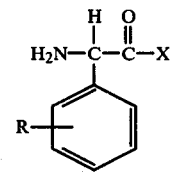

wherein R represents —H, —OH, —NO$_2$, a halogen atom (e.g., —F, —Cl, —Br) a lower C$_{1-6}$ alkyl group (e.g., methyl, ethyl, amyl, hexyl, a lower C$_{1-6}$ alkoxy group, or a lower C$_{1-6}$ hydroxy-alkyl group (e.g., hydroxy-methyl) and wherein X represents either —OH or —NH$_2$. The R substituents are preferably in the para position on the benzene ring.

For this separation process, the Schiff base is preferably formed from the corresponding benzaldehyde of the general formula

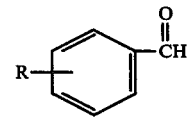

wherein R has the same meaning stated above.

In general, the process of this invention can also be utilized with other aldehydes or ketones, provided they satisfy the following requirements:

1. They readily form a water-insoluble Schiff base of the phenylglycine amide;
2. The Schiff bases thus formed readily decompose, without decomposition of the aldehyde or ketone;
3. The Schiff bases and the aldehyde or ketone are stable under the process conditions;
4. There must be a distinct difference as regards the solubility in water and in organic solvents between the Schiff base of the phenylglycine amide and that of the phenylglycine or the phenylglycine acid itself.

Benzaldehyde and substituted benzaldehydes are the only compounds which most satisfactorily meet all of these conditions.

For instance, the process can be carried out with e.g., cyclohexanone, but in this case the yields will be distinctly lower, and cyclohexanone will be partly consumed due to side-condensation reactions.

The reaction with benzaldehyde, for the simultaneous formation of Schiff base, can be carried out at temperatures of 0° to 60° C., preferably at temperatures of about 25° to 45° C. The pH of the reaction mixture should lie between 7 and 12, preferably between about 8 and about 11. If, in the formation of the Schiff base benzaldehyde is used in low amounts of e.g. 1 to 2 and preferably 1.0 to 1.5 moles of aldehyde per mole of the optically active phenylglycine amide without application of another solvent for the Schiff base of the amide, a deposit of the Schiff base of optically active phenylglycine amide is obtained. The optically active phenylglycine and/or its Schiff base has then dissolved as salt in the mother liquor. If an excess of benzaldehyde is applied, the benzaldehyde will act not only as a reactant, but also as a solvent, and two layers will be obtained. It is also possible to use, for the extraction, mixtures of benzaldehyde and other solvents, such as mixtures with toluene, chloroform, benzene and tetrachloroethylene.

The recovery of the optically active phenylglycine or the phenylglycine amide as the case may be from the corresponding Schiff base can be performed in a simple way by acidification of the Schiff base with nearly any acid of the strength of at least organic carboxylic acids (e.g., acetic acid, propionic acid, toluenesulfonic acid), but is preferably effected with a strong mineral acid, (such as sulphuric, hydrochloric, phosphoric acid), which causes the Schiff base to decompose. For hydrolysis of the α-phenylglycine amide Schiff bases, it is preferred to use a strong mineral or organic acid (sulfuric or toluenesulfonic acid) so that this reaction is conducted at a pH level below about 3. In this way, simultaneous hydrolysis of the phenylglycine amide to phenylglycine can be effected in one step. This latter step can also be usefully effected at sub-atmospheric pressure.

If the decomposition of the Schiff base is carried out at temperatures of up to approximately 100° C., no racemization will take place. Use of a temperature of approximately 90° C. to 110° C. during the decomposition and the subsequent hydrolysis has the advantage that the benzaldehyde is simultaneously distilled off. If the decomposition is carried out at temperatures exceeding about 120° C., the optically active phenylglycine or phenylglycine amide will at least partially racemize. In the case where D-phenylglycine is the primarily desired product, the decomposition of the Schiff base of the L-phenylglycine may intentionally be carried out at an elevated temperature, e.g., at about 120° to 150° C., in order to obtain racemic DL-phenylglycine for recycle to the process.

The Schiff base-forming reaction is preferably carried out in an aqueous medium.

The invention will now be further elucidated with the aid of the following Examples.

EXAMPLE I

A suspension of 3.0 g (0.02 moles) of D-α-phenylglycine amide, 3.0 g (0.02 moles) of L-α-phenylglycine and 2.2 ml of concentrated ammonia (0.03 moles) in 100 ml of water contained in a flask is adjusted to a pH of 10.6 by means of a 5 N sodium hydroxide solution, with simultaneous stirring. To this solution 4.0 ml of benzaldehyde (0.04 moles) is slowly added at 30° C., with simultaneous stirring.

During the addition of benzaldehyde, the pH is maintained at 10.6. After 10 hours of stirring at room temperature, the crystalline deposit which forms is separated off by filtration, and the deposit on the filter is washed twice with 25 ml portions of water. The yield of the Schiff base of D-α-phenylglycine amide (D-N-benzylidene-α-phenylglycine amide) amounts to 4.6 grams, which corresponds to 97% of the theoretical yield (melting point 138°-139° C.).

The resulting D-α-phenylglycine amide Schiff base is introduced into 60 ml of 3.6 N sulphuric acid, and 30 ml of water-benzaldehyde distillate is distilled off at 100° C. under 1 atmosphere pressure. The remaining solution is then boiled for an additional hour at atmospheric pressure. After cooling this solution to room temperature, the pH is adjusted to 5.6 by means of concentrated ammonia. Crystalline D-α-phenylglycine forms and is separated off by filtration and twice washed on the filter with 10 ml portions of water.

The amount of D-α-phenylglycine thus obtained is 2.7 grams (yield: 90%). Specific rotation of the D-α-phenylglycine:

$[\alpha]_D^{20} = -157.2°$ C. (C=1.0; 1.0 N HCl)

EXAMPLE II

A solution of 6.0 g of D-α-phenylglycine amide (0.04 moles), 6.0 g of L-α-phenylglycine (0.04 moles) and 3.0 ml of concentrated ammonia (0.04 moles) in 200 ml of water, which has a temperature of 37° C. and a pH of 10.5, is stirred with the addition of 50 ml of benzaldehyde. Two liquid layers were formed, the benzaldehyde layer was drawn off, and the aqueous layer solution is once more stirred with addition of another 50 ml of benzaldehyde.

The benzaldehyde extracts thus obtained are combined and washed with 100 ml of 3.6 N sulphuric acid. After the sulphuric acid extract has been separated off, 40 ml of the water-benzaldehyde mixture is removed by distillation at 100° C., under atmospheric pressure.

The remaining residue is boiled for an additional one hour at atmospheric pressure. After cooling to room temperature, the residue is adjusted to a pH of 5.0 by addition of concentrated aqueous ammonia. The crystallized D-α-phenylglycine thus formed is filtered off and twice washed on a filter with 10 ml portions of water.

The amount of D-α-phenylglycine obtained after drying is 5.2 grams (yield: 87%). Specific rotation of this D-α-phenylglycine is:

$[\alpha]_D^{20} = -157.0°$ (C=1.0; 1.0 N HCl)

The aqueous layer at a pH 10.5 separated as described above from the benzaldehyde layer is adjusted to a pH of 2.0 by addition of concentrated sulphuric acid.

Next, a distillate of 100 ml of water-benzaldehyde mixture is distilled off therefrom at 100° C., under atmospheric pressure. After cooling to room temperature, the remaining mixture is adjusted to a pH 6, by addition of concentrated ammonia, with simultaneous cooling.

The thus-crystallized L-α-phenylglycine is recovered by filtration and twice washed on the filter with 10 ml portions of water.

The amount of L-α-phenylglycine thus obtained is 5.6 g (yield: 93%). Specific rotation:

$[\alpha]_D^{20} = +157.1°$ (C=1.0; 1.0 N HCl)

EXAMPLE III 6.0 g of D-α-phenylglycine amide (0.04 moles), 6.0 g of L-α-phenylglycine (0.04 moles) and 4 ml of concentrated ammonia (0.056 moles) contained in a flask is adjusted to pH 10.7 at 40° C. by means of 5 N sodium hydroxide solution, with simultaneous stirring. Next, 4.7 ml of benzaldehyde (0.045 moles) is slowly added at 40° C. The pH then drops to 9.9. Stirring is continued for another half hour, in which period the temperature drops to 30° C.

The resulting suspension is centrifuged and rewashed with two 50 ml portions of water. Upon drying at 50° C. and 12 mm Hg, 9.0 g of the Schiff base, i.e., D-N-benzylidene-α-phenylglycine amide is obtained (yield: 95%). Melting point 139° C. Specific rotation:

$[\alpha]_D^{20} = -82.5$ (C=1.0; 99% formic acid).

EXAMPLE IV

In a flask provided with a stirrer and containing a suspension of 2.5 g (13.7 mgmoles) of D-α-p-methoxy phenylglycine amide, 3.5 g (19.7 mgmoles) of L-α-p-methoxy phenylglycine and 1.0 ml (13.7 mgmoles) of concentrated ammonia (25% wt.), there is added 5 N NaOH at 40° C.—with simultaneous stirring—until the pH equals 10.5. To this solution 1.7 ml (17 mgmoles) of benzaldehyde is added with simultaneous stirring. The pH then drops to 9.9. After stirring for another 1¼ hours at 30° C., the suspension is filtered over a glass-filter and washed on the filter with two 50 ml portions of water. After drying the crystals for two hours at 50° C., and 12 mm Hg pressure, the yield of the Schiff base, i.e., D-N-benzylidene-α-p-methoxy phenylglycine amide is 3.5 g (yield: 95.4%). Melting point 139°-140° C. Specific rotation:

$[\alpha]_D^{20} = -78.9°$ (C=1.0; 99% wt. of formic acid)

3.2 g (12.0 mgmoles) of this Schiff base is absorbed in 50 ml of 3.6 N sulphuric acid. After 25 ml of the water-benzaldehyde mixture has been distilled off at 98°-100° C., the remainder is boiled for another hour. After cooling to room temperature, the pH is adjusted to 5.2 by means of concentrated ammonia (25% wt.). The crystallized D-α-p-methoxy phenylglycine formed is filtered off and washed on the filter with two 10 ml portions of water and, after that, with two 10 ml portions of acetone.

The amount of D-α-p-methoxy phenylglycine thus obtained, upon drying at 50° C., and 12 mm Hg, is 2.0 g (yield: 92.6%). Specific rotation:

$[\alpha]_D^{20} = -154.8°$ (C=0.8; 1.0 N HCl)

EXAMPLE V

The process of Example I was repeated except that the last step of distillation of the water-benzaldehyde mixture after treatment with sulfuric acid, was conducted at 200 mm pressure. The same results were obtained.

EXAMPLE VI

The procedure of example II is repeated, this time however 4.9 milliliters of p.methoxybenzaldehyde (0.04 moles) are used and the reaction mixture is stirred for 15 hours. In this manner 9.9 g of the Schiff base, i.e. D-N-p.methoxybenzylidenephenylglycine amide, is obtained (yield 92.4%). The melting point is 69° C. and the specific rotation $[\alpha]_D^{20}$ (C=1.0 in 99% formic acid) is −55.0°.

It will be noted that in the Examples the amount of benzaldehyde ranged from approximately equimolar with respect to the amide (Examples III and VI), to substantially equimolar with respect to both the glycine acid and the amide, to a substantial excess (Example II, using approximately 6 moles of benzaldehyde per total moles of acid and amide). The use of lesser amounts of aldehyde will cause the conversion of only the amide to the Schiff base; the use of more than equimolar amounts of aldehyde (with respect to the glycine amide) will enhance formation of the glycine acid Schiff base and also, when in excess, provide the extraction solvent as described above (and see Example II).

Because racemization may be substantially completely avoided by the process of this invention, the optical purity of the separated products is essentially limited only by the optical purity of the components in the starting mixture.

What is claimed is:

1. A process for the recovery while substantially completely avoiding simultaneous racemization of optically active α-phenylglycine amides from mixtures thereof with the corresponding optically active α-phenylglycine acid, wherein said glycine compounds are of the formula:

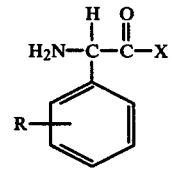

wherein R represents —H, —OH, —NO₂, a halogen atom, a lower $C_{1-6}$ alkyl group, a lower $C_{1-6}$ alkoxy group, or a lower $C_{1-6}$ hydroxy-alkyl group, and wherein X represents either —OH or —NH₂; which process comprises treating said mixture with a Schiff base-forming benzaldehyde of the formula:

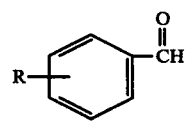

wherein R has the same meaning stated above; to form at least the Schiff base of said amide, and thereafter separating said amide Schiff base from the glycine acid compound or its Schiff base by the solubility difference therebetween at a temperature insufficient to cause any substantial racemization thereof and decomposing the Schiff base or bases with liberation of the benzaldehyde.

2. The process of claim 1, wherein said R group represents the same substituent in both the glycine compounds and in the benzaldehyde compound.

3. The process of claim 1, wherein D-α-phenylglycine amide is separated from L-α-phenylglycine using benzaldehyde.

4. The process of claim 1, wherein D-α-(p-methoxyphenyl)glycine amide is separated from L-α(p-methoxyphenyl)glycine acid using benzaldehyde.

5. The process of claim 1, wherein D-α-(p-methoxyphenyl)glycine amide is separated from L-α-(p-methoxyphenyl)glycine acid using p-methoxybenzaldehyde.

6. The process of claim 1, wherein the formation of said Schiff base is effected at a pH between about 8 and about 11.

7. The process of claim 1, wherein said Schiff base-forming compound is used in an amount of 1 to 2 moles per mole of said amide, and the resulting amide Schiff base compound is separated as a precipitate.

8. The process of claim 1, wherein said Schiff base-forming compound is used in molar excess, and said amide Schiff base is separated by extraction into said excess.

9. The process of claim 1, wherein said Schiff base is formed in an aqueous medium.

10. The process of claim 1 including the further step of decomposing the separated amide Schiff base to form the corresponding free optically active α-phenylglycine amide.

11. The process of claim 10, wherein said Schiff base is decomposed at a pH below about 3, whereby the corresponding free optically active α-phenylglycine acid is obtained.

* * * * *